United States Patent [19]
Saperstein et al.

[11] 4,230,883
[45] Oct. 28, 1980

[54] PREPARATION OF HYDROXYPHENYLALANINE HYDROHALIDE SALTS

[75] Inventors: David D. Saperstein, Mountainside; Seemon H. Pines, Murray Hill, both of N.J.

[73] Assignee: Merck & Co., Inc., Rahway, N.J.

[21] Appl. No.: 859,415

[22] Filed: Dec. 12, 1977

[51] Int. Cl.$^2$ .................... C07C 99/00; C07C 101/72
[52] U.S. Cl. .................................... 562/445; 562/444
[58] Field of Search ................ 260/519; 562/444, 445, 562/446

[56] References Cited

U.S. PATENT DOCUMENTS

| | | | |
|---|---|---|---|
| 2,868,818 | 1/1959 | Pfister et al. | 260/519 |
| 3,158,648 | 11/1964 | Jones et al. | 260/519 |
| 3,830,836 | 8/1974 | Soichiro et al. | 260/519 |
| 3,832,388 | 8/1974 | Lorenz | 260/519 |

OTHER PUBLICATIONS

Merck Index, 8th Ed., pp. 684 (1968).
Merck Index 9th, p. 790, #5925 (1976).

*Primary Examiner*—Natalie Trousof
*Assistant Examiner*—James H. Reamer
*Attorney, Agent, or Firm*—Gabriel Lopez; Daniel T. Szura; Harry E. Westlake, Jr

[57] ABSTRACT

The invention relates to the hydrohalide salts of L-α-methyl-3,4-dihydroxyphenylalanine (methydopa). The method of preparing these and related compounds in the absence of water or other polar solvents is also shown.

7 Claims, No Drawings

PREPARATION OF HYDROXYPHENYLALANINE HYDROHALIDE SALTS

BACKGROUND OF THE INVENTION

U.S. Pat. No. 2,868,818 discloses the hydrochloride and hydrobromide salts of compounds having the general formulae:

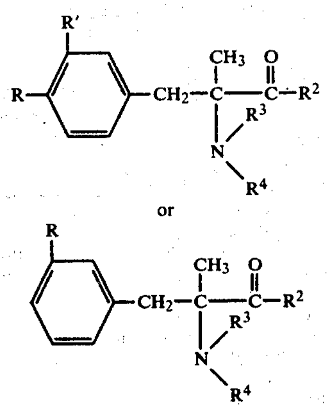

wherein R' is hydrogen, hydroxy, or an alkoxy or acyloxy group having a chain length of from one to four carbon atoms; R is hydroxy, or an alkoxy or acyloxy group having a chain length of from one to four carbon atoms; $R^2$ is a hydroxy, amido, or a lower alkoxy group; and $R^3$ and $R^4$ are hydrogen, or lower alkyl or acyl.

The Merck Index, 8th Ed., Merck & Co., Inc., Rahway, N.J. (1968), at page 684 listed methyldopa hydrochloride.

SUMMARY OF THE INVENTION

The invention comprises the 1:1 microcrystalline hydrohalide salts of L-α-methyl-3,4-dihydroxyphenylanine (methydopa) and the method for producing them and related compounds by the use of liquid HCl or HBr as both solvent and acid.

DETAILED DESCRIPTION

The novel compounds of the invention are L-isomer 1:1 microcrystalline salts having the formula:

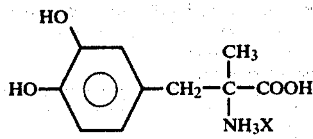

I where X is chloro or bromo, substantially free of impurities.

These compounds are antihypertensive agents. Because of their improved solubility characteristics, they are superior to methyldopa itself and to the methyldopa "salt" described in the art.

Although U.S. Pat. No. 2,868,818 generically teaches the hydrohalide salts of α-methylhydroxyphenylalanines and the Merck Index, 8th Ed. specifically mentions the hydrochloride of methyldopa, if one uses the methods taught in the art (e.g., U.S. Pat. No. 2,868,818, col. 5, lines 65 to 69) for the production of these hydrohalide salts, there is produced amorphous compounds containing from about 65% to about 85% of the theoretical salt content. Hydrogen halide as used herein is limited to hydrogen chloride and bromide. A salt solution containing a 1:1 ratio of hydrogen halide and hydroxyphenylalanine can be made; however, attempts to produce the 1:1 solids represented by formula I have failed. Significantly, the Merck Index, 9th Ed. has dropped the reference to methyldopa hydrochloride.

The term 1:1 salt as used herein means a solid compound consisting essentially of equimolar amounts of hydrogen halide and a hydroxyphenylalanine.

"Salts" (actually, mixtures) with less than the theoretical, stochiometric 1:1 ratio of acid to hydroxyphenylalanine do not show the same properties as the 1:1 microcrystalline salts. For example, when 1 g of methyldopa hydrochloride prepared by the prior art methods is added to 1 ml of $H_2O$ at room temperature some of the compound does not dissolve, whereas most dissolves rapidly. When 1 g of the 1:1 microcrystalline salt prepared by the method of the instant invention is added to 1 ml of $H_2O$, all the material dissolves, although more slowly than the 65–85% mixture. The 65–85% mixture is much more hygroscopic than the 1.1 microcrystalline salt. The 1:1 microcrystalline salt extinguishes polarized light, whereas the 65–85% mixture does not.

For therapeutic administration, the 1:1 salt is a preferred material because reproducible solutions can be prepared easily. If a solution of the prior art "salt" is prepared, the amount of active compound in solution would depend on the quality of the mixture and the amount of time devoted to making the solution.

In a typical preparation according to the known methods, hydrogen halide as a gas or in solution is added to a slurry of methyldopa in water, alcohol, or other appropriate solvent. The slurry is allowed to mix until a clear solution is obtained. The solvent is then removed by an applied vacuum or other means leaving a white solid. Although it is expected to find a 1:1 salt by this procedure, analysis shows that the affinity of the hydrogen halide is strong for the solvent. Hence, removal of the solvent prevents the formation of the 1:1 microcrystalline salt by removing part of the acid along with the solvent. The prior art methods can be used for the production of some hydroxyphenylalanine hydrohalide 1:1 salts, but not for the methyldopa salt.

The novel process of this invention is the use of liquid HCl or HBr as both solvent and acid to produce a 1:1 microcrystalline acid salt of formula III. The reaction mixture must be substantially free (>98%) of water and other polar solvents. It is preferred that the mixture be at least 99% free. Removal of excess acid leaves the 1:1 microcrystalline salt substantially free (>98%) of impurities, e.g., solvent or free amino acid. The process may be shown as follows:

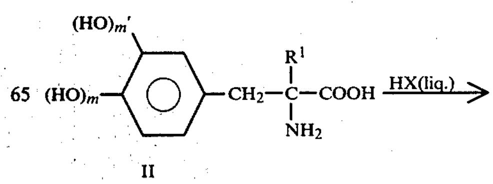

II

-continued

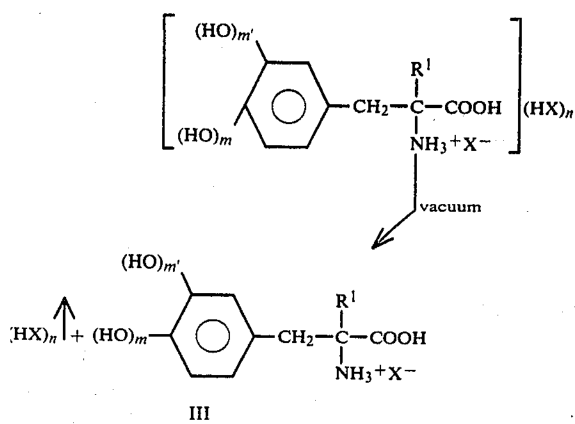

where
1 indicates an excess of acid over 1:1,
$R^1$ is H or alkyl of one through four carbons,
X is chloro or bromo, and
n and m' are independently zero or one but not both zero.

The compounds of formula II are known and are useful for a variety of applications including antihypertension, catecholamine inhibition, tyrosine hydroxylase inhibition, activity on the central nervous system, and for the treatment of Parkinson's disease. Although not every compound exhibits each of the stated activities, these can readily be ascertained by those skilled in the art. The 1:1 microcrystalline salts of formula III have the same uses as the formula II compounds but have additional advantages because of their increased solubility in water and other polar solvents.

The reaction is carried out with substantially anhydrous reagents at a temperature range of −85° C. to 0° C. under autogenous pressure. At 0° C., the pressure is approximately 420 lbs. for HCl. The reaction is allowed to proceed to dissolution (approximately 1–10 minutes) in an acid resistant vessel (e.g., glass lined), after which the excess HX is vented and finally pumped off under vacuum. The amount of excess HX is not critical and is used to facilitate dissolution of the amino acid.

The formula I, II, and III compounds have a chiral center and may occur in optically active forms, i.e., as optical isomers. These isomers are designated conventionally by the symbols L and D, + and −, l and d, S and R, or sometimes combinations thereof. Where the compound name or formula has no isomer designation, the name or formula includes the individual isomer, mixtures thereof, and racemates.

The L-isomer is preferred.

The hydrochloride salt is preferred.

The following examples are given by way of illustration and are not to be construed as limiting.

All temperatures are in degrees Celsius.

TLC refers to thin layer chromatography.

EXAMPLE 1

Methyldopa hydrochloride 250 g of dried (KF<0.1%) methyldopa are dissolved in an excess (ca. 250 ml) of anhydrous, liquid HCl at 0° in a glass-lined bomb. The solution is stirred for 5–10 minutes. Most of the excess HCl is then vented through $CaCl_2$. The residual HCl is then pumped off under vacuum at 25°. 600 g of methyldopahydrochloride, a microcrystalline product, are recovered which have the following characteristics:

infrared peak at 1718 $cm^{-1}$
$[\alpha]_{546}^{25}$: +140.3 (c=0.5% w/v in 0.25 M Cu $SO_4$@pH 3.4).
TLC: single spot (n-butanol/$H_2O$/$CH_3COOH$/acetone/benzene; 1:1:1:1:1)
Titration for $Cl^-$: 14.22%
Calc'd.: 14.31%
Equivalent Weight: 98.9% of theory
KF: 0.3%

Following the procedure of example 1 but substituting the aminoacids of Table 1 for methyldopa, the corresponding microcrystalline 1:1 hydrochloride salts of Table 2 are prepared.

TABLE 1

| | |
|---|---|
| 1. | L-α-ethyldopa |
| 2. | L-α-butyldopa |
| 3. | α-methyl-4-hydroxyphenylalanine (α-methyltyrosine) |
| 4. | L-α-methyltryosine |
| 5. | α-sec-butyltyrosine |
| 6. | α-propyl-3-hydroxyphenylalanine |
| 7. | L-3-hydroxyphenylalanine |
| 8. | L-tyrosine |
| 9. | L-dopa |

TABLE 2

| | |
|---|---|
| 1. | L-α-ethyldopahydrochloride |
| 2. | L-α-butyldopahydrochloride |
| 3. | α-methyltyrosinehydrochloride |
| 4. | L-α-methyltyrosinehydrochloride |
| 5. | α-sec-butyltyrosinehydrochloride |
| 6. | α-propyl-3-hydroxyphenylalaninehydrochloride |
| 7. | L-3-hydroxyphenylalaninehydrochloride |
| 8. | L-tyrosinehydrochloride |
| 9. | L-dopahydrochloride |

Following the procedure of example 1 but substituting HBr for HCl and the amino acids of Table 1 for methyldopa, the corresponding microcrystalline 1:1 hydrobromide salts of Table 3 are prepared.

TABLE 3

| | |
|---|---|
| 1. | l-α-ethyldopahydrobromide |
| 2. | L-α-butyldopahydrobromide |
| 3. | α-methyltyrosinehydrobromide |
| 4. | L-α-methyltyrosinehydrobromide |
| 5. | α-sec-butyltyrosinehydrobromide |
| 6. | α-propyl-3-hydroxyphenylalaninehydrobromide |
| 7. | L-3-hydroxyphenylalaninehydrobromide |
| 8. | L-tyrosinehydrobromide |
| 9. | L-dopahydrobromide |

What is claimed is:

1. A process for preparing a 1:1 microcrystalline salt product of the formula:

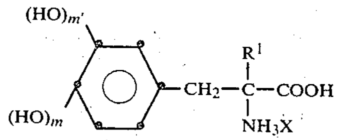

wherein
m and m' are independently zero or one but not both zero,
X is chloro or bromo, and
$R^1$ is H or alkyl of one through four carbons which comprises reacting amino acid the formula:

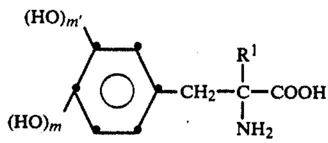

with liquid HBr or HCl, the reactants being substantially free of water and other polar solvents, such that said product consists essentially of equimolar amounts of said amino acid and HBr or HCl, substantially free of impurities.

2. The process of claim 1 wherein $R^1$ is methyl, and the hydrogen halide of HCl.

3. The process of claim 2 wherein the amino acid is α-methyl-3,4-dihydroxyphenylalanine.

4. The process of claim 3 wherein the amino acid has the L-configuration.

5. The process of claim 2 wherein the amino acid is α-methyl-4-hydroxyphenylalanine.

6. The process of claim 2 wherein the amino acid is α-methyl-3-hydroxyphenylalanine.

7. The process of claim 2 where the reaction mixture is at least 99% free of water and other polar solvents.

* * * * *